United States Patent
Karst et al.

(10) Patent No.: US 7,028,537 B2
(45) Date of Patent: Apr. 18, 2006

(54) COUPLING ELECTROCHEMISTRY TO MASS SPECTROMETRY AND HIGH PERFORMANCE LIQUID CHROMATOGRAPHY

(75) Inventors: Uwe Karst, Muenster (DE); Georg Diehl, Muenster (DE); Heiko Hayen, Muenster (DE)

(73) Assignee: ESA Biosciences, Inc., Chelmsford, MA (US)

( * ) Notice: Subject to any disclaimer, the term of this patent is extended or adjusted under 35 U.S.C. 154(b) by 437 days.

(21) Appl. No.: 10/245,176

(22) Filed: Sep. 17, 2002

(65) Prior Publication Data

US 2003/0062475 A1   Apr. 3, 2003

Related U.S. Application Data

(60) Provisional application No. 60/323,552, filed on Sep. 20, 2001.

(51) Int. Cl.
*G01N 30/02* (2006.01)

(52) U.S. Cl. .................. 73/61.55; 73/61.52; 73/61.58; 422/70; 436/161; 436/173; 210/656

(58) Field of Classification Search ............... 73/61.52, 73/61.55, 61.56, 61.58; 422/70; 436/161, 436/173; 210/656
See application file for complete search history.

(56) References Cited

U.S. PATENT DOCUMENTS 4,343,767 A * 8/1982 Long et al. ................. 422/70
5,399,256 A * 3/1995 Bohs et al. ................. 204/409

OTHER PUBLICATIONS

"Liquid chromatography with post-column electrochemical treatment and mass spectrometric detection of non-polar compounds" Diehl et al., *Analyst*, 2001 126, 288-290.

"Electrospray as a Controlled-Current Electrolytic Cell: Electrochemical Ionization of Neutral Analytes for Detection by Electrospray Mass Spectrometry" Van Berkel Zhou *Analytical Chemistry*, vol. 67, No. 21 Nov. 1, 1995 p. 3958-3964.

"On-Line Investigation of the Generation of Nonaqueous Intermediate Radical Cations by Electrochemistry/Mass Spectrometry" Zhang and Brajter-Toth *Anal Chem.*, 2000, 72, 2533-2540.

"On-Line Probe for Fast Electrochemistry/Electrospray Mass Spectrometry. Investigation of Polycyclic Aromatic Hydrocarbons" Xu et al. *Anal. Chem*, 1996, 68, p. 4244-4253.

"Electrochemical Polymerization of Aniline Investigated Using On-Line Electrochemist Electrospray Electrospray Mass Spectrometry" Deng and Van Berkel *Anal. Chem*, 1999, 71, p. 4284-4293.

"Electrochemically Modulated Preconcentration and Matrix Elimination for Organic Analytes Coupled On-Line with ElectrosprayMass Spectrometry" Pretty et al. *Anal Chem.*, 72, p. 2066-2074.

(Continued)

*Primary Examiner*—Daniel S. Larkin
(74) *Attorney, Agent, or Firm*—Hayes Soloway P.C.

(57) ABSTRACT

A hyphenated technique based on the combination of high performance liquid chromatography (HPLC), electrochemical (coulometric) oxidation (EC) and electrospray ionization (ESI)- or atmospheric pressure chemical ionization (APCI)-mass spectrometry (MS), allows access of selected groups of low and medium polarity analytes to ESI- or APCI-mass spectrometry after HPLC by electrochemical treatment of the sample.

11 Claims, 5 Drawing Sheets

OTHER PUBLICATIONS

"The ESA electrical cell coupled with electrospray ionization mass spectrometry" U. Jurva Poster presented 990616 at the 47th ASMS Conference on Mass Spectrometry and Allied Topics, Dallas, TX.

"Electrochemistry On-Line with Electrospray: Insights into Oxidative Metabolism of Tamoxifen" Deng and Van Berkel Chemical and Analytical Sciences Division, Oak Ridge National Laboratory Oak Ridge, TN 37831-6365, 2 pg. independent article.

"Comparison of Detection Limits of Electrochemistry/Electrospray-MS and APCI-MS" Zhang and Cole, Department of Chemistry, University of New Orleans, Lakefront New Orleans, LA 70148, 2pg independent article.

"An Electrochemical Cell for On-Line Electrochemistry/Mass Spectrometry" Corazon et al. *Anal. Chem.*, 1997, 69, p. 5067-5072.

"Electrochemistry On Line with Mass Spectrometry Insight into Biological Redox Reactions" Volk et al. *Anal. Chem.*, 1992, 64, p. 21A-33A.

"Effect of Mobile Phase Composition on the Electrochemical Cell Conversion Efficiency in Electrochemistry/Mass Spectrometry" Regino et al., *Analytica Chimica Acta*, 369, 1998, p. 253-262.

"Detection of the Oxidative Produces of 3-Hydroxykynurenine Using High-Performance Liquid Chromatology-Electrochemical Detection- Ultraviolet Absorption Detection-Electron Spin Resonance Spectrometry and High-performance Liquid Chromatography- Electrochemical Detection-Ultraviolet absorption detection-Mass Spectrometry" Iwahashi and Ishii, *Journal of Chromatography A*, 773, 1997, p. 23-31.

"3-Hydroxyanthranillc Acid-Derived Compounds Formed Through Electrochemical Oxidation" Iwahashi, *Journal of Chromatography B*, 736, 1999, p. 237-245.

"Electrochemical Thermospray Mass Spectrometry Instrumentation for Coupling Electrochemistry to Mass Spectrometry" Hambitzer et al., *Analytical Chemistry* 70, 1998, p. 838-842.

"A Role for Electrospray Mass Spectrometry in Electrochemical Studies" Bond et al., *Anal. Chem.* 67, 1995, p. 1691-1695.

"In Vetro Mimicry of Metabolic Oxidation Reactions by Electrochemistry/ Mass Spectrometry" Jurva et al., *Rapid Commun. Mass Spectrum* 14, 2000, p. 529-533.

"Characterization of Solution-Phase and Gas-Phase Reactions in On-Line Electrochemistry-Thermosprey Tandem Mass Spectrometry" Volk et al., *Journal of Chromatography* 474, 1989, p. 231-243.

"In Vitro Mimicry of Metabolic Oxidation Reactions by Electrochemistry/Mass Spectrometry" Poster presented at the 15th IMS Conference in Barcelona 28/8-31/8 2000, Jurva et al.

"On-Line Electrochemistry/Thermospray/Tandem Mass Spectrometry as a New Approach to the Study of Rodox Reaction: The Oxidation of Uric Acid" Volk et al., *Anal. Chem.* 61, 1989, p. 1709-1717.

"Electrochemical Oxidation and Nucleophillic Addition Reactions of Metallocenes in Electrospray Mass Spectrometry" Xu et al., *Anal. Chem.* 66, 1994, p. 119-125.

"On-Line Linear Sweep Voltammetry-Electrospray Mass Spectrometry" Lu et al., *Anal. Chem.* 69, 1997, p. 2478-2484.

"Electrochemistry/Thermospray/Tandem Mass Spectrometry In the Study of Biooxidation of Purines" Correspondence *Anal Chem.* 60, 1988, p. 720-724.

"Electrochemistry Combined On-Line with Electrospray Mass Spectrometry" Zhou et al., *Anal Chem.* 67, 1995, p. 3643-3649.

"Electrochemically Modulated Liquid Chromatography Coupled On-Line with Elecyrospray Mass Spectrometry" Deng et al., *Anal Chem.* 72, 2000, p. 2641-2647.

* cited by examiner

FIG. 1

Setup of the HPLC/Electrochemistry/MS-System

FIG. 2

FIG. 3
SIM Chromatograms at Different Potentials of the Coulometric Cell

FIG. 4

| Analyte | ESI interface | | | | APCI interface | | | |
|---|---|---|---|---|---|---|---|---|
| | LOD/mol dm$^{-3}$ | LOQ/mol dm$^{-3}$ | Linear range/mol dm$^{-3}$ | RSD ($n$ = 5) $c$ = $\times$ 10$^{-6}$ mol dm$^{-3}$ | LOD/mol dm$^{-3}$ | LOQ/mol dm$^{-3}$ | Linear range/mol dm$^{-3}$ | RSD ($n$ = 3) $c$ = $\times$ 10$^{-6}$ mol dm$^{-3}$ |
| Methyl FCE | 4 × 10$^{-7}$ | 1 × 10$^{-6}$ | 5 × 10$^{-7}$–5 × 10$^{-5}$ | 4.9% | 1 × 10$^{-8}$ | 3 × 10$^{-8}$ | 2 × 10$^{-8}$–3 × 10$^{-6}$ | 2.7% |
| Ethyl FCE | 3 × 10$^{-7}$ | 9 × 10$^{-7}$ | 5 × 10$^{-7}$–1 × 10$^{-4}$ | 6.6% | 2 × 10$^{-8}$ | 6 × 10$^{-8}$ | 2 × 10$^{-8}$–3 × 10$^{-6}$ | 2.4% |
| Biphenyl FCE | 1 × 10$^{-8}$ | 3 × 10$^{-8}$ | 1 × 10$^{-8}$–5 × 10$^{-5}$ | 5.4% | 2 × 10$^{-8}$ | 6 × 10$^{-8}$ | 2 × 10$^{-8}$–9 × 10$^{-6}$ | 3.6% |
| Benzylphenyl FCE | 3 × 10$^{-9}$ | 9 × 10$^{-9}$ | 5 × 10$^{-9}$–5 × 10$^{-5}$ | 4.3% | 1 × 10$^{-8}$ | 3 × 10$^{-8}$ | 2 × 10$^{-8}$–3 × 10$^{-6}$ | 6.0% |
| 4-Bromo-4'-biphenyl FCE | 4 × 10$^{-9}$ | 1 × 10$^{-8}$ | 5 × 10$^{-9}$–1 × 10$^{-4}$ | 4.8% | 4 × 10$^{-8}$ | 1 × 10$^{-7}$ | 7 × 10$^{-8}$–9 × 10$^{-6}$ | 20.2% |
| 4-n-Octylphenyl FCE | 4 × 10$^{-9}$ | 1 × 10$^{-8}$ | 5 × 10$^{-9}$–1 × 10$^{-5}$ | 3.7% | 1 × 10$^{-8}$ | 3 × 10$^{-8}$ | 2 × 10$^{-8}$–9 × 10$^{-6}$ | 3.8% |
| 4-n-Nonylphenyl FCE | 8 × 10$^{-9}$ | 2 × 10$^{-8}$ | 1 × 10$^{-8}$–5 × 10$^{-5}$ | 1.8% | 1 × 10$^{-8}$ | 3 × 10$^{-8}$ | 2 × 10$^{-8}$–9 × 10$^{-6}$ | 6.5% |

FIG. 5

HPLC/Electrochemistry/MS for the Selective Determination of Alcohols and Phenols … (page text continues)

COUPLING ELECTROCHEMISTRY TO MASS SPECTROMETRY AND HIGH PERFORMANCE LIQUID CHROMATOGRAPHY

CROSS REFERENCE TO RELATED APPLICATIONS

This application claims priority benefit of U.S. Provisional Application Ser. No. 60/323,552, filed Sep. 20, 2001.

FIELD OF THE INVENTION

This invention relates to chemical analysis of sample products, and more particularly to the coupling of an electrochemical cell (EC), a high performance liquid chromatography (HPLC), and mass spectrometry system (MS).

BACKGROUND OF THE INVENTION

The hyphenation of high performance liquid chromatography (HPLC) and mass spectrometry (MS) enables the selective and sensitive determination of various groups of analytes, because it combines the advantages of an effective separation technique and a highly selective detection method. Due to increased robustness of the instrumentation, HPLC-MS has become a widely used analytical technique in research and routine analysis.

However, some problems remain which are mainly caused by the difficulty of coupling a separation taking place in liquid phase with a detection technique that relies on the formation of gas phase ions. Different designs of interfaces have been developed to overcome this obstacle. Currently, the most common interfaces are electrospray ionization (ESI) and atmospheric pressure chemical ionization (APCI). HPLC-MS measurements with ESI and APCI have been reported to show excellent results for the determination of ionic or polar analytes, because these either are already ionized or can easily be ionized under the comparably soft conditions used for both ESI and APCI. Ionization typically occurs by protonation or deprotonation, but coordination of the analyte with other ions may also be used. Analytes of lower polarity are less accessible to the ESI or APCI processes resulting in low ionization efficiencies and losses in sensitivity. The scope of HPLC-MS on polar analytes is, however, unfortunate considering that analytes of lower polarity are best suited for separation by reversed phase liquid chromatography.

To overcome this limitation, only few attempts for the efficient ionization of less polar analytes have been done. Cole et al. in their *Analytical Chemistry* article used the electrospray interface for the electrochemical oxidation (ionization) of metallocenes. Another research group connected an electrochemical cell to thermospray-MS to study the electrooxidation of N,N-dimethylaniline. Brajter-Toth et al. used a combination of an electrochemical cell and particle beam mass spectrometry in a report in *Analytical Chemistry*. Also, the coupling of electrochemistry and thermospray-MS was applied by Brajter-Toth et al. for oxidative studies on uric acid. Van Berkel and co-workers have reported in *Analytical Chemistry* the determination of alcohols in saw palmetto fruit extracts and of alcohols and phenols in the oils of cloves, lemon, rose and peppermint using electrospray as an electrochemical reactor following a derivatization step with ferrocene-based reagents. Another approach suggested by Van Berkel et al. was the online coupling of different electrochemical flow cells with ESI-MS, either floated at or decoupled from the electrospray high voltage. Although the coupling of an electrochemical flow cell with MS gave promising results, no attempts for using this system after HPLC separation have been done.

Because the derivatization of alcohols and phenols with ferrocene-based reagents, e.g., can easily be accomplished and the resulting products should be well suited for electrochemical oxidation as well as for reversed phase liquid chromatography, we propose a new HPLC-electrochemistry-MS technique that has utility, e.g., for the determination of ferrocene derivatives.

SUMMARY OF THE INVENTION

A powerful new hyphenated technique based on the combination of HPLC, electrochemical (coulometric) oxidation and ESI- or APCI-MS has been developed. This technique is a simple and efficient method of allowing accessing to a selected group of low and medium polarity analytes to ESI or APCI mass spectrometry after reverse-phase HPLC. Post-column electrochemical (EC) treatment leads either to the oxidation or reduction of the analyte, depending on the applied potential. Thus, charged or strongly polar reaction products are formed, which are compatible with ESI and/or APCI mass spectrometry. A coulometric three-electrode arrangement is selected to achieve almost quantitative electrochemical conversion. For this HPLC-EC-MS hyphenation, the electrochemical cell is inserted between column and mass spectrometer without need for further technical modification of the system.

DETAILED DESCRIPTION OF THE INVENTION

Figure 1:
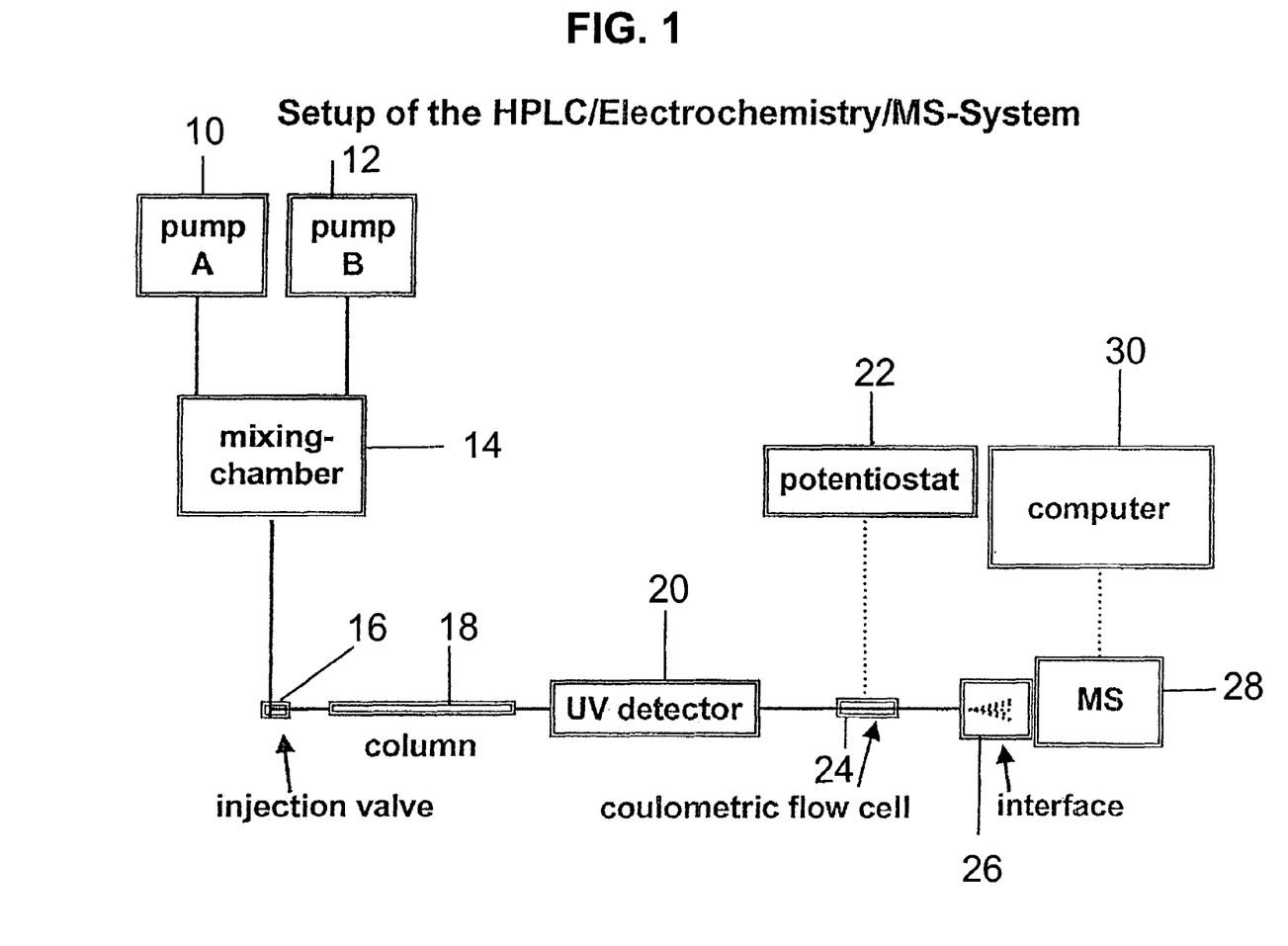
FIG. 1 is a schematic assembly of an HPLC-electrochemistry-MS system in accordance with the present invention.

FIG. 1 shows a schematic assembly of the HPLC-electrochemistry-MS system. The HPLC component includes pumps 10, 12 that provide a steady high pressure to the system. This is needed to force the sample through the stationary phase. Connected to the pumps is a mixing chamber 14 for homogenizing the mobile phase. From the mixing chamber, the sample flows into the injector valve 16, which injects it into the separation column 18. The different components of the mixture are separated out because they pass through the column at different rates due to differences in their shape, size, polarity, etc. Additionally, other types of columns, such as guard columns, can be inserted before the separation column 18. Once through the column 18, the sample moves into the UV/vis detector 20 (which could be another detector in alternative embodiments, e.g., a fluorescence detector).

Figure 5:
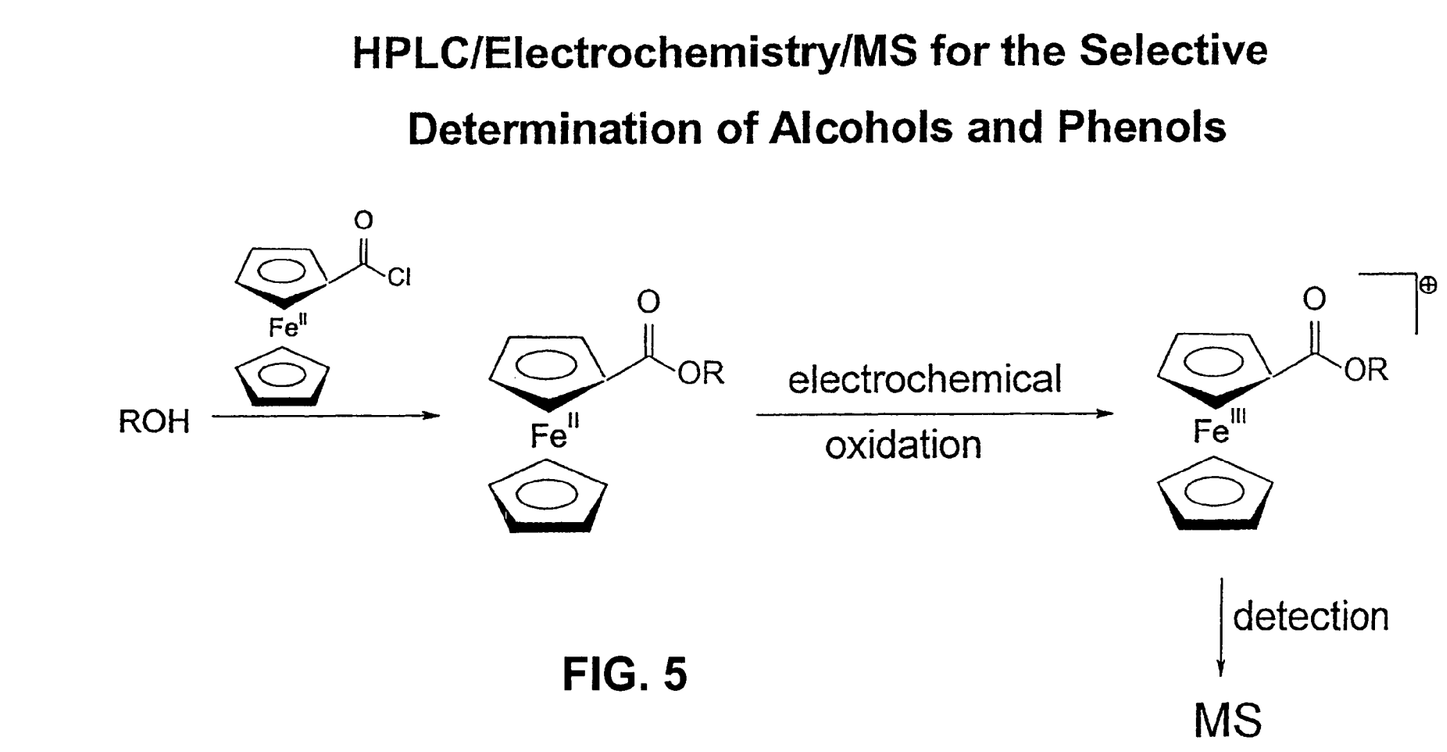
FIG. 5 shows the chemical derivatization and the electrochemical oxidation of the products for selective determination of Alcohols and Phenols.

After detection, the sample leaves the HPLC part of the system and enters the coulometric flow cell 24. In the coulometric flow cell, the sample is electrochemically (EC) treated which leads either to the oxidation or reduction of the analyte, depending on the applied potential. Thus, charged or strongly polar reaction products are formed, which are compatible with ESI and/or APCI mass spectrometry. FIG. 5 shows an example of this process. Referring again to FIG. 1, a potentiostat 22 is used to control the potential applied to the electrochemical cell, and, in certain embodiments, may additionally be used to measure the resulting current in the flow cell 24. After the post-column electrochemical conversion, the sample moves into the ionization interface 26 used to couple liquid chromatography to mass spectrometry. The interface can be either electrospray ionization (ESI) or atmospheric pressure chemical ionization (APCI). Finally, the sample is analyzed with the mass spectrometer 28. The computer 30 is used to store the result and control the process.

EXAMPLE 1

Analysis of Phenothiazines

With this setup, phenothiazine and eleven of its derivatives were separated by means of HPLC and oxidized in the coulometric flow cell, The oxidation products were identified using the described HPLC-EC-MS system both with ESI and APCI. Phenothiazine and its derivatives are characterized by low ionization potentials as could be demonstrated by cyclic voltammerty. Radical cations are formed as intermediates; further oxidation leads to the sulfoxides. The stability of the radical cation strongly varies. For phenothiazine, a stable radical cation is observed by mass spectrometry, while the radical cations of its derivatives having a substituent in position 10 are characterized by low stability. Compared with the derivatives, which are characterized by basic side chains (easy protonation), the ionization yield for phenothiazine using ESI and APCI in the positive mode is poor. For phenothiazine, limits of detection could be improved from 1 µmol/l for HPLC-APCI-MS to 10 nmol/l for HPLC-EC-APCI-MS under comparable conditions. The linear range comprised three decades. Within the linear range of calibration, a relative standard deviation (n=3) of 2–6% was observed. The experimental method and results are described in detail in the following section.

EXAMPLE 2

Analysis of Ferrocene-Derivatized Alcohols and Phenols

First, ammonium formate and all alcohols and phenols used were purchased from Aldrich Chemie (Steinheim, Germany) in the highest quality available. Formic acid was obtained from Fluka (Buchs, Switzerland). Solvent for HPLC was acetonitrile LiChroSolv gradient grade from Merck (Darmstadt, Germany). Ferrocene carboxylic acid chloride (FCC) was synthesized and was characterized by H-NMR, El-MS and IR.

The derivatives of ferrocene carboxylic esters (FCEs) were synthesized. Fifty milligrams ($2 \times 10^{-4}$ mol) of FCC and 73.3 mg ($2 \times 10^{-4}$ mol) 4-dimethylaminopyridine (DMAP) were dissolved in 2 ml dichloromethane and added to a solution of $1.82 \times 10^{-4}$ mol alcohol or phenol in 2 ml dichloromethane. The mixture was left to react until the dark red coloration weakened. The DMAP and the excess of FCC were removed by separation on an aluminum oxide microcolumn (30 mm×5-mm id). The ferrocene carboxylic acid esters were eluted with 3-ml dichloromethane, dried under nitrogen and characterized by EI-MS.

The HPLC-MS system from Shimadzu (Duisburg, Germany) consisted of a SCL-10 Avp controller unit, DGU-14A degasser, two LC-10ADvp pumps, SUS mixing chamber (0.5 ml), SIL-10A autosampler, SPD-I0AV UV/vis detector, LCMS QP8000 single quadrupole mass spectrometer with electrospray ionization and atmospheric pressure chemical ionization probes and Class 8000 Version 1.11 software.

The electrochemical system from ESA, Inc. (Chelmsford, Mass.) consisted of GuardStat potentiostat and model 5021 conditioning cell. The conditioning cell contains a glassy carbon coulometric working electrode, a Pd counter electrode, and a $Pd/H_2$ reference electrode. All potentials are given vs. $Pd/H_2$.

Because the ESI interface tolerates only HPLC flow rates of 02 ml $min^{-1}$ or less and the APCI interface works best with flow rates of 0.3 ml $min^{-1}$, columns of different inner diameter and different LC flow rates and injection volumes were used for optimum performance. All separations were performed using Discovery C18 columns (Supelco, Deisenhofen, Germany) equipped with guard columns of the same material with the following dimensions: 5 µm particle size, 100 Å pore size, 2.1 mm id (for ESI experiments) and 3.0 mm id (for APCI experiments), 20 mm length (guard column) and 150 mm (analytical column). Eluent A of the mobile phase was a solution of 250 mg ammonium formate and 0.6 ml formic acid in 1 L deionized water (pH=3). Eluent B was acetonitrile. A binary gradient at flow rates of 0.25 ml $min^{-1}$ (2.1 mm id column for ESI) and 0.6 ml $min^{-1}$ (3.0 mm id column for APCI) with the following profile was used:

| t/min | 0.01 | 3 | 8 | 18 | 20 | 25 | 25.5 |
|---|---|---|---|---|---|---|---|
| [$CH_3CN$](%) | 60 | 60 | 90 | 90 | 60 | 60 | stop |

The injection volume was 5 µl (2.1 mm id column) and 10 µl (3.0 mm id column).

For all measurements with the MS system, curved desolvation lines (CDL) voltage –35 V, CDL temperature 300° C., deflector voltages 35 V and detector voltage 1.7 kV were used. The ESI parameters were probe voltage +2.5 kV and nebulizer gas flow-rate 4.5-ml $min^{-1}$. APCI experiments were carried out with probe voltage 0 V, nebulizer gas flow-rate 2.5 ml $min^{-1}$ and probe temperature 350° C.

The online coupling of the electrochemical cell to HPLC-MS was accomplished by inserting a coulometric flow cell for quantitative oxidation between the UV/vis detector and the interface of the MS system (FIG. 1). The connection between the flow cell and the interface was kept as short as possible to reduce loss of ions during transport. To prevent electrical connection between ESI interface and coulometric cell via the eluent, appropriate ground connection has to be assured. The MS parameters were adjusted to the conditions imposed by HPLC binary gradient elution.

Figure 2:
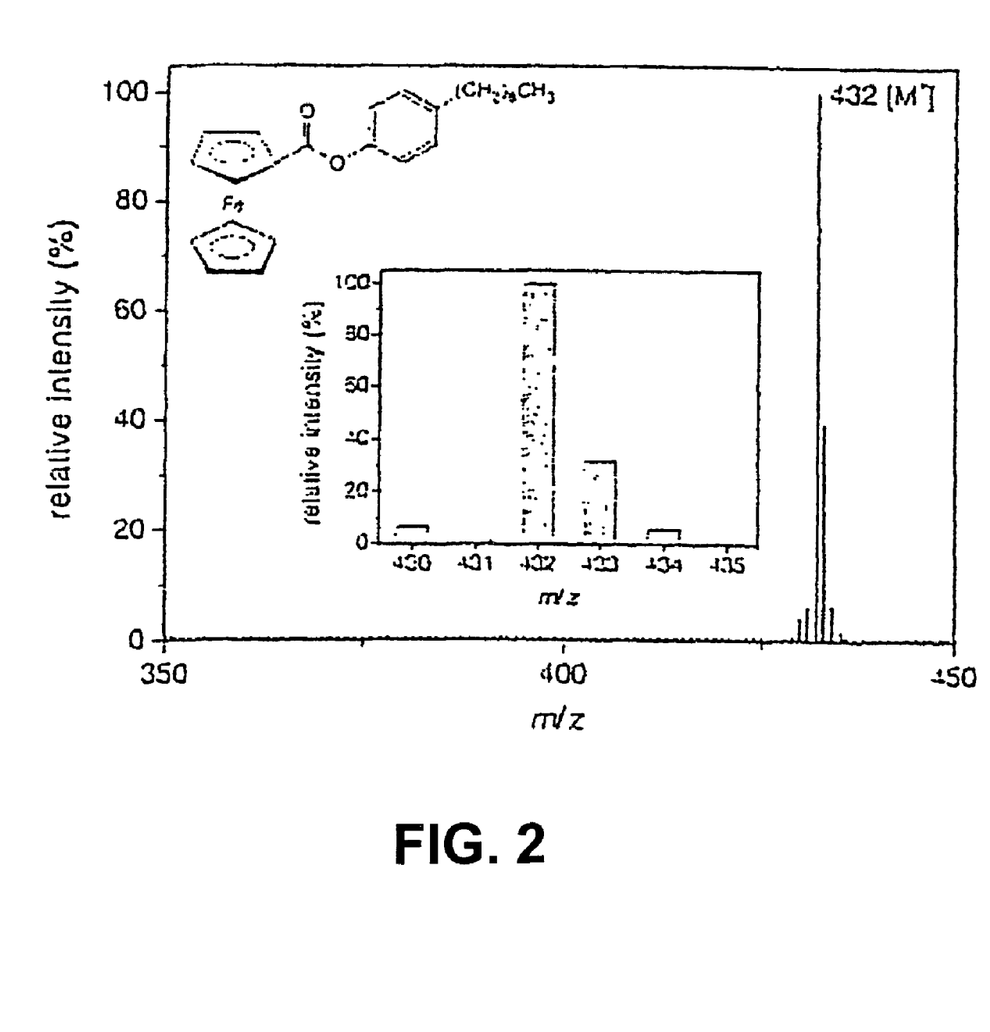
FIG. 2 is a plot of the electrochemistry (cell voltage=0.7 V)–APCI (APCI voltage=0 V) mass spectrum of $1 \times 10^{-5}$ mol dm$^{-3}$ solution of 4-n-nonylphenyl ferrocene carboxylic acid ester (FCE) with the calculated isotope pattern for $C_{26}H_{32}Fe$, chemical structure of 4-n-nonylphenyl FCE inserted inside of the figure, in accordance with the present invention.

The mass spectrum of 4-n-nonylphenyl FCE recorded with this HPLC-electrochemistry-MS system using the APCI interface is shown in FIG. 2. The APCI probe voltage was set to 0 V for these measurements to ensure that ions which are observed in the spectrum are generated by the oxidative potential of 700 mV in the coulometric cell and not by the APCI process. The interface may, therefore, be considered as being a heated nebulizer interface. This experiment was not possible with the ESI interface, because the spraying process of ESI depends on a high voltage at the ESI capillary. The base peak in the spectrum of m/z=432 corresponds to the molecular ion of 4-n-nonylphenyl FCE. The isotope pattern in the spectrum fits well to the calculated isotope pattern. The corresponding spectrum recorded with the ESI interface (probe voltage of +2.5 kV) is almost identical and is therefore not shown. The appearance of the molecular ion peak shows that the oxidation of Fe(II) in the ferrocene function to Fe(III) in the corresponding ferrocenium ion was successfully accomplished by electrochemical oxidation in the coulometric flow cell.

Figure 3:
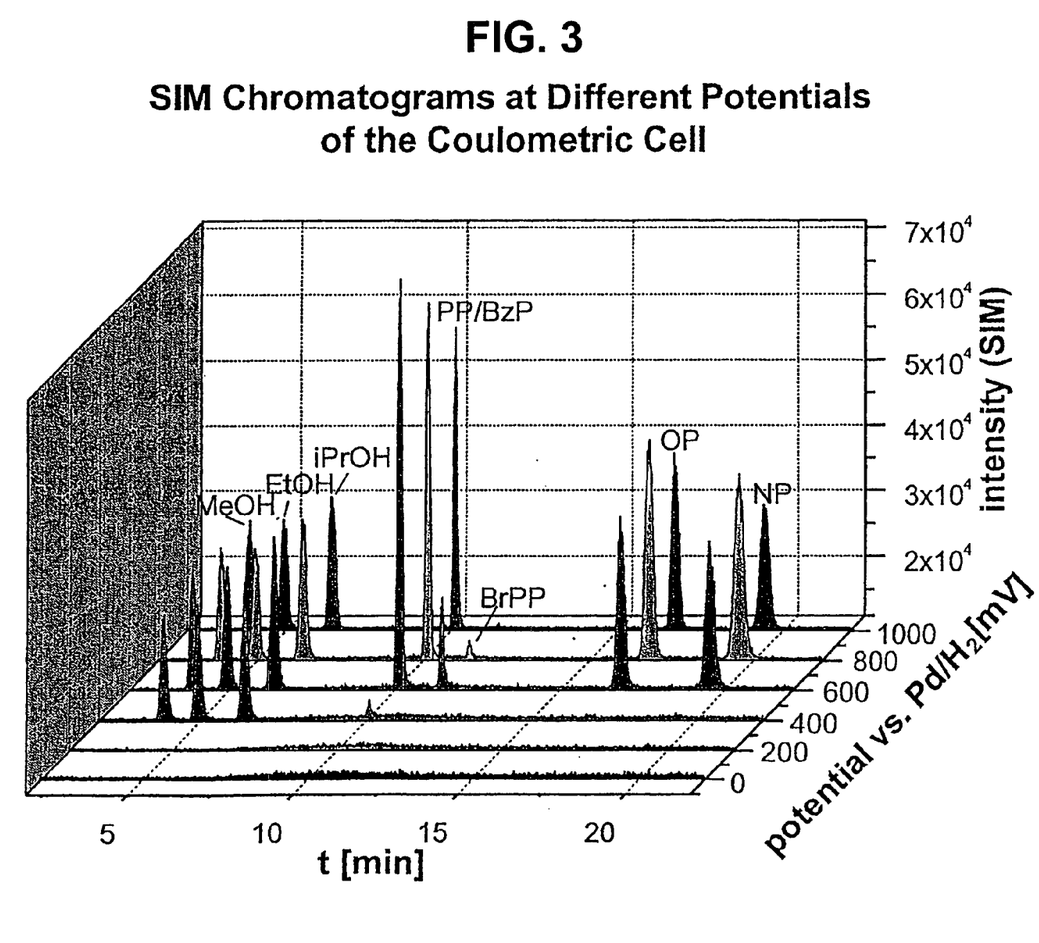
FIG. 3 are a series of HPLC-electrochemistry-APCI-MS chromatograms at different coulometric cell potential, recorded in SIM mode (m/z=244.0, 258.0, 272.1, 382.1, 396.1, 460.0, 418.2, 432.2), APCI potential 0 V (MeOH=methyl FCE, EtOH=ethyl FCE, iPrOH=I-propyl FCE, PP=4-biphenyl FCE, BnP=4-benzylphenyl FCE, BrPP=4-brom-4'-biphenyl FCE, OP=4-n-octylpheny FCE, NP=4-n-nonylphenyl FCE), in accordance with the present invention.

Further proof for this assumption is provided in FIG. 3 showing chromatograms (raw data, no smoothing of the peaks) of the separation of a $1\times10^{-5}$ mol dm$^{-3}$ mixture of different FCEs recorded as total ion current (TIC) in the selected ion monitoring (SIM) mode. For these measurements, different potentials ranging from 0 to 1000 mV vs. Pd/H$_2$ were applied to the coulometric flow cell. No peaks are detected at potentials below 400 mV. Beginning with a potential of 400 mV, molecular ions of the short chain FCEs as well as of the coeluting 4-biphenyl and 4-benzylphenyl FCEs produce clearly detectable peaks. At a potential of 600 mV, all compounds in the mixture are oxidized to the corresponding ferrocinium ions and can be seen in the chromatogram. It can be observed that the peak areas of 4-biphenyl, 4-benzylphenyl and 4-bromo-4'-biphenyl FCE are lowered for higher potentials than 600 mV. The optimum potential for this mixture of FCE derivatives was found to be 700 mV vs. Pd/H$_2$. Therefore, a cell voltage of 700 mV was used for all following experiments.

There are two major advantages of this technique when compared to the electrochemical oxidation in the ESI interface. The oxidative potential in the electrochemical flow cell can be adjusted precisely to the requirements for the analysis. Analytes that are more easily oxidized than interfering substances could be selectively ionized. The high voltage used in the electrospray interface cannot be adjusted to the requirements of the oxidative process and it is nor possible to gain knowledge about the exact oxidative potential within the ESI capillary.

The large surface of the glassy carbon-working electrode in the coulometric flow cell enables quantitative turnover rates in the oxidation process resulting in increased sensitivity and a large linear concentration range. The electrochemical set-up in the ESI interface is more similar to a thin layer amperometric cell, which has oxidation efficiencies of typically less than 20%. Although the oxidation in the electrospray process might be quantitative at very low concentrations and/or very low flow rates, good linearity cannot be expected.

The additional coupling of HPLC to electrochemistry and MS adds selectivity because of the chromatographic separation. Preformed ions, for example, will elute before the more unpolar analytes and cannot interfere or suppress the analytes mass signals.

Figure 4:
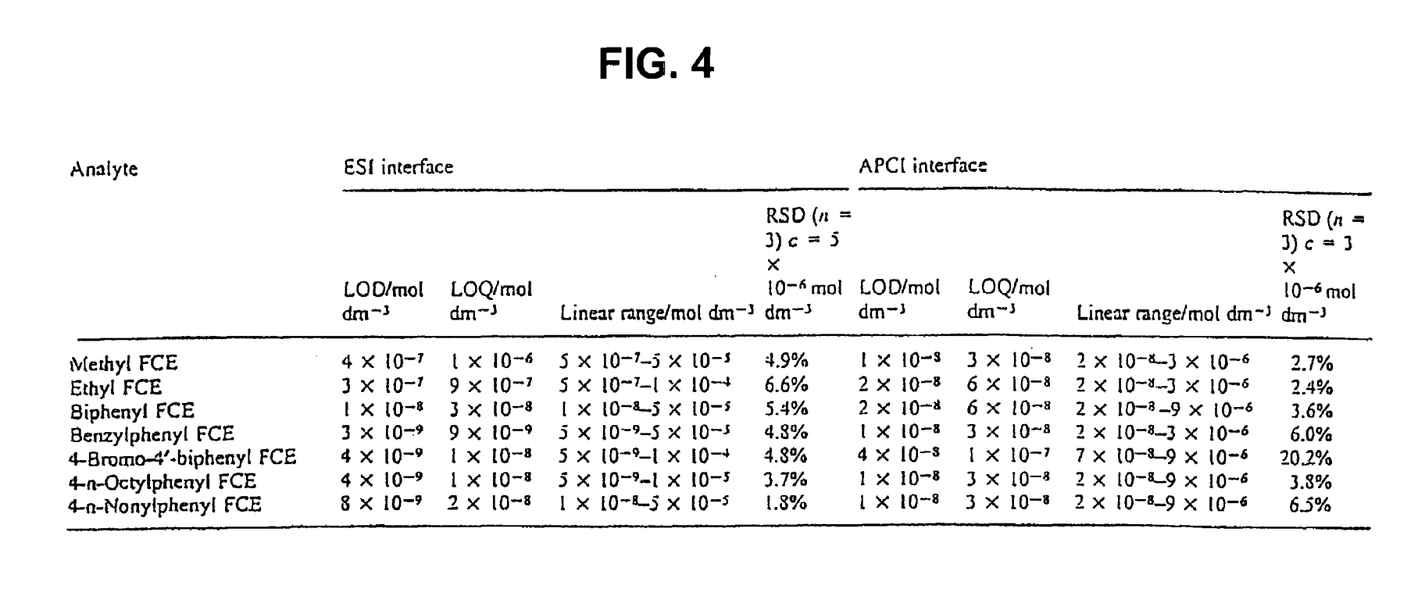
FIG. 4 is a table of analytical figures of merit for selected FCEs (LOD=limit of detection, LOQ=limit of qualification, RSD=relative standard deviation), in accordance with the present invention.

Calibration data were then recorded with the HPLC electrochemistry-MS system and both ESI and APCI interfaces. The calibration functions exhibited excellent linearities in the lower concentration ranges, but smaller than expected peak areas for higher concentrations when using the APCI mode (FIG. 4). This can be explained by insufficient oxidation in the flow cell at higher concentration levels and the increased HPLC flow rate used for APCI. This reduces the linear concentration range for the APCI mode compared to the ESI mode. For ESI, linear ranges of four decades are observed for selected analytes.

Analytical figures of merit for both interfaces are also provided in FIG. 4. Obviously, ESI allows for lower limits of detection and larger linear concentration ranges than APCI for the phenol derivatives, whereas the short chain aliphatic alcohol FCEs can be detected at lower concentration in the APCI mode. In the ESI mode, it was obvious that the limits of detection differed strongly between the derivatives of alcohols and phenols. To investigate if this effect is due to the different composition of the mobile phase in the course of the applied gradient, thus resulting in different spray conditions in the interface, isocratic elution was applied as well. However, the same results were obtained as for gradient elution. The reproducibility of both methods ranges from 1.8 to 6.6% (n=3), except for the detection of 4-bromo-4'-biphenyl FCE in the APCI mode and could be further lowered by the use of an internal standard.

The foregoing embodiments are intended to be illustrative and not limiting. Numerous other embodiments will be apparent to those skilled in the art. All such alternative embodiments are included in the broad principle of the invention, as defined in the following claims.

The invention claimed is:

1. A method for analyzing a sample solution containing electrochemically active compounds comprising:
    passing said sample solution through a liquid chromatography column for achieving time-spaced separation of materials eluting from the column;
    passing materials eluting from said liquid chromatography column through a coulometric electrochemical flow cell for electrochemically converting said eluding materials to charged materials; and
    passing eluent from the electrochemical flow cell to a mass spectrometer and measuring materials contained in the sample by mass spectrometry.

2. A method as claimed in claim 1, further comprising the step of passing eluent from the liquid chromatography column through an UV detector, and measuring the sample in the UV detector.

3. A method as claimed in claim 1, further comprising electrochemically measuring electrochemically active fluids in said flow cell.

4. A method according to claim 1, wherein said step of passing said sample solution through said liquid chromatography column comprises reverse phase high performance liquid chromatography.

5. A method according to claim 1, further comprising subjecting said eluent to an ionization interface comprising electrospray ionization or atmospheric pressure chemical ionization.

6. A system for measuring sample solutions containing electroactive materials, said system comprising a high performance liquid chromatography system outputting an eluent;

a coulometric electrochemical flow cell receiving the eluent and electrochemically converting materials in said eluent to charged materials; and a mass spectrometry system receiving eluent outputted from the electrochemical flow cell.

7. A system as claimed in claim 6, further comprising a photodetector receiving eluent prior to the receipt of said eluent by said mass spectrometry system.

8. A system as claimed in claim 7, wherein said photodetector is a UV/vis detector.

9. A system according to claim 6, wherein said high performance liquid chromatography system comprises: a separation column, an injection system for injecting a sample into said separation column, and a detector for measuring separation of said sample.

10. A system according to claim 6, further comprising an ionization interface disposed between said liquid chromatography system and mass spectrometry system.

11. A system according to claim 10, wherein said ionization interface comprises an electrospray ionizer or an atmospheric pressure chemical ionizer.

* * * * *